(12) United States Patent
Helfenbein et al.

(10) Patent No.: US 8,936,465 B2
(45) Date of Patent: Jan. 20, 2015

(54) METHOD AND DEVICE FOR PROGRAMMING A CORDLESS HANDPIECE FOR ROOT CANAL TREATMENT

(75) Inventors: Gerald Helfenbein, Gilgenberg (AT); Stefan Putz, Oberndorf (AT); Rainer Schröck, Bürmoos (AT)

(73) Assignee: W&H Dentalwerk Bürmoss GmbH, Bürmos (AT)

( * ) Notice: Subject to any disclaimer, the term of this patent is extended or adjusted under 35 U.S.C. 154(b) by 480 days.

(21) Appl. No.: 12/646,576

(22) Filed: Dec. 23, 2009

(65) Prior Publication Data

US 2010/0161955 A1    Jun. 24, 2010

(30) Foreign Application Priority Data

Dec. 24, 2008    (EP) .................................... 08022455

(51) Int. Cl.
| | | |
|---|---|---|
| *A61C 1/02* | (2006.01) | |
| *A61C 1/00* | (2006.01) | |
| *A61C 3/00* | (2006.01) | |
| *A61C 1/10* | (2006.01) | |
| *A61C 1/07* | (2006.01) | |
| *A61C 3/03* | (2006.01) | |
| *A61C 3/08* | (2006.01) | |
| *G06F 1/24* | (2006.01) | |
| *G06F 9/00* | (2006.01) | |
| *G06F 3/00* | (2006.01) | |
| *A61C 5/02* | (2006.01) | |

(52) U.S. Cl.
CPC ........................................ *A61C 5/02* (2013.01)
USPC ............... 433/28; 433/27; 433/114; 433/123; 713/100; 710/8

(58) Field of Classification Search
USPC .................................................... 433/27, 123
See application file for complete search history.

(56) References Cited

U.S. PATENT DOCUMENTS

| | | | | |
|---|---|---|---|---|
| 4,180,812 A | * | 12/1979 | Kaltenbach et al. ............ | 433/28 |
| 5,295,833 A | | 3/1994 | Chihiro et al. | |
| 7,965,851 B2 | * | 6/2011 | Bengtsson ....................... | 381/60 |

(Continued)

FOREIGN PATENT DOCUMENTS

| | | |
|---|---|---|
| DE | 195 20 765 A1 | 12/1995 |
| DE | 195 20 765 B4 | 7/2004 |

(Continued)

OTHER PUBLICATIONS

European Search Report for EP08022455 (mailed May 25, 2009).

(Continued)

*Primary Examiner* — Ernest Unelus
*Assistant Examiner* — Ronald Modo
(74) *Attorney, Agent, or Firm* — Klarquist Sparkman, LLP

(57) ABSTRACT

A method and device for programming a cordless handpiece used for root canal treatment and having a first memory and a tool holder for a treatment tool are described. The method includes providing a first data volume having a plurality of data sets in a second memory separate from the first memory, each of the data sets comprising at least one parameter assigned to the cordless handpiece and/or to the operable tool, selecting at least some of the data sets from the first data volume in the second memory, transmitting the selected data sets from the second memory to the first memory of the handpiece, and selecting a data set from the updated first memory for operation of the handpiece.

26 Claims, 1 Drawing Sheet

(56) References Cited

U.S. PATENT DOCUMENTS

| | | |
|---|---|---|
| 2003/0195642 A1* | 10/2003 | Ragnini .................. 700/56 |
| 2005/0042572 A1* | 2/2005 | Katsuda et al. ............ 433/98 |
| 2008/0254404 A1* | 10/2008 | Heraud .................. 433/27 |
| 2008/0293008 A1* | 11/2008 | Regere et al. ............ 433/119 |
| 2009/0271016 A1* | 10/2009 | Wampler et al. ............ 700/96 |

FOREIGN PATENT DOCUMENTS

| | | | |
|---|---|---|---|
| DE | 10 2007 020100 | 10/2008 | |
| EP | 788778 A2 * | 8/1997 | ............... A61C 1/00 |
| EP | 1172071 A2 * | 1/2002 | ............... A61C 1/00 |
| JP | 08000640 | 1/1996 | |
| JP | 2003159262 | 6/2003 | |
| JP | 2006334416 | 12/2006 | |

OTHER PUBLICATIONS

Office Action from Japanese Patent Office for JP2009290327 (mailed Oct. 8, 2013).

* cited by examiner

METHOD AND DEVICE FOR PROGRAMMING A CORDLESS HANDPIECE FOR ROOT CANAL TREATMENT

CROSS REFERENCE TO RELATED APPLICATION

The present application claims priority from pending European Patent Application No. 08022455 filed Dec. 24, 2008, which is incorporated herein by reference.

BACKGROUND

1. Field

This application relates to a method and a device for programming a cordless medical or dental handpiece for root canal treatment.

2. Description of Prior Art

Conventional cordless devices for root canal treatment have at least one cordless handpiece and a charger. The cordless handpiece is equipped with a drive motor and a battery for supplying power to the motor, in addition to a tool holder for a treatment tool. A measurement circuit for measuring the root canal length and/or the load applied to the tool is preferably also provided in the handpiece. In measuring the root canal length, the treatment tool retained in a tool holder is used as an electrode and is electrically connected to the root canal length measuring circuit via a contact piece provided in the head of the handpiece or externally on the handpiece. If the control arrangement of the measurement circuit indicates that the tool has reached a target position in a root canal or that a predefined torque has been exceeded, it automatically stops the tool or automatically rotates it in the opposite direction. Because of the anatomy of the root canal to be treated, a plurality of different tools, in particular files of different diameters and tool properties, e.g., breaking strengths, must be used to prepare a root canal. These tools thus differ significantly with regard to their parameters to be set, e.g., the maximum allowed rotational speed or torque.

Such a medical or dental device, and the method for adjusting the cordless handpiece with the parameters of the treatment tool for root canal treatment are known from DE 19520765 B4.

The device for root canal treatment known from the prior art having at least one cordless handpiece and one charger has a plurality of adjusting elements for adjusting the handpiece to the respective parameters of the tool being used. The different adjusting elements, in particular for adjusting the rotational speed, the maximum allowed torque and the autofunction parameters, e.g., autostop or autoreverse, may be provided on both the cordless handpiece and the charger. The user may thus adjust his handpiece to the parameters of the tool being used by means of the plurality of adjusting elements.

One disadvantage of this prior art approach has proven to be the manual adjustment of the individual tool and handpiece parameters by means of the plurality of adjusting elements on the handpiece or on the charger.

Operation of the cordless device for root canal treatment is complex and time-consuming due to the numerous tool parameters, e.g., the maximum rotational speed, the maximum torque or the numerous handpiece parameters, e.g., the autofunction parameters (such as autostop or autoreverse, in which the tool automatically rotates in the opposite direction or stops when the tool has reached a certain position in the root canal or when a certain load is applied to the tool). Due to the number of parameters, each time a tool is changed, the user must adjust the handpiece to comply with the new tool and handpiece parameters. To do so, the user must operate the numerous adjusting elements on the handpiece and/or on the charger.

In addition, the device known in the prior art for root canal treatment entails the risk of possible error sources. Due to the numerous parameters to be adjusted, there is the risk that the user might set possible values incorrectly, resulting in complications in treatment of the root canal, e.g., breakage of the file in the root canal because the torque limits for the tool being used are set too high.

SUMMARY

Described below are embodiments of a method and a device for programming a cordless handpiece for root canal treatment that will make it possible to avoid or at least reduce the disadvantages of the prior art, and to program a cordless handpiece easily and with the exclusion of possible error sources.

According to one exemplary embodiment of a method for programming a cordless handpiece used for root canal treatment, having a first memory and a tool holder for a treatment tool, the handpiece is programmed by providing a first data volume having a plurality of data sets in a second memory, each of the data sets comprising at least one parameter assigned to the cordless handpiece and/or the treatment tool to be operated, selecting at least some of the data sets from the first data volume in the second memory, transmitting the selected data sets from the second memory to the first memory of the handpiece and selecting, manually or automatically, a data set from the updated first memory for operation of the handpiece.

The second memory is separate from the first memory of the handpiece. The second memory may be in a base station (which can be designed as a charger for the battery operated handpiece), or configured as a separate memory element.

Each of the data sets may comprise at least one tool parameter for a tool, such as for a dental file used to treat a root canal, and/or a handpiece parameter. A designation, such as a name of each respective file, can be assigned to each data set. The user can preselect one or more desired files, for example, the files commonly used by the user, from a library provided in the second memory, which may contain, e.g., all of the data sets, such as data sets of all the files available on the market. The user may then make his preselection of data sets from the library, such as by using at least one control element, to which end he selects the data sets according to which files are desired, which may be which files he uses especially often or which files he needs for the next treatment. Then, a data volume, which may be a partial data volume comprising at least one data set, or a total data volume, is transferred to the memory of the handpiece. This is done by establishing a connection between the handpiece with the first memory and the second memory, or by connecting only the first memory itself. The first memory may be configured as a memory card having contacts, or as any other suitable memory element. Then, e.g., using at least one control element, the user can select the appropriate data set, e.g., the name of the file, which is used.

The at least one control element for selection of the partial data volume or a data set can be configured as a pushbutton, potentiometer, joystick, proximity sensor, touchscreen display or other element for selecting from among a plurality of parameters. In one embodiment, the at least one control element preferably has multiple functions for menu guidance in the file library, e.g., "left," "right," "up" and "down" functions as well as an actuation function, such as "ok." In addition, further control elements may be provided on the handpiece or on the base station for parameters including both the tool and the handpiece, e.g., an on/off switch for the root canal length measurement circuit or a torque reducing switch for difficult anatomy, reducing all set torques by 5% to 20%.

To ensure a complete first data volume for all the files available on the market, the first data volume must be updated regularly to include all new files and their parameters as a data set. This is made possible by transmission of the existing data sets and the new data sets, or only the new data sets, from a third memory to the second memory. To do so, the third memory, which can be configured as a memory card, USB stick, Smart Media card, memory stick, multimedia card or Secure Digital memory card (SD card or mini-SD card), is connected to the second memory via a suitable interface and the data sets are transmitted. In another embodiment, data may also be transmitted by wireless data transmission (e.g., via radiofrequency, infrared, inductive or capacitive data transmissions) from the third memory to the second memory.

As an alternative to storage of the first data volume in a second memory, such as in a base station, the first data volume may also remain in the third memory, which thus serves to update the first data volume. The handpiece is thus programmed directly by transmission of the appropriate data sets from the third memory, in particular from a memory card. The total data volume then remains in the third memory.

Selection of the partial data volume, i.e., of one or more of the data sets, is made by at least one control element, which is arranged on or connected to the handpiece itself, the second memory or the third memory. The user thus programs his handpiece with only the data sets relevant for him.

The selection of a data set from the updated first memory may be made manually by the user via at least on control element or automatically. Automatic selection can be accomplished with a tool identification circuit, which may use one or more of: radiofrequency waves (RFID), a barcode on the tool and a reader on the handpiece, at least one sensor on the handpiece and identification on the basis of a magnetic field generated, and determination of the tool material, the material thickness or the material hardness. In this embodiment, the user need only make a preselection of the dental tools (i.e., files in this example) available for use. All additional steps in programming the handpiece are then performed automatically.

The present method and device for programming a cordless handpiece provide a number of significant advantages. Rapid and simple operation for the user is ensured by providing a first data volume having a plurality of data sets appropriate for each tool and handpiece that may be used. It is no longer necessary to manually set each parameter for the tool and/or the handpiece before operation of each operation tool on the handpiece or on a base station. This yields time savings for the user in programming the presettings of the tool and the handpiece as well as minimizing the control elements for adjusting the various parameters.

In addition, possible error sources are at least minimized if not entirely prevented by the present method and device on the basis of finished data sets and data sets coordinated with the tool and handpiece. Through manual or automatic selection of finished data sets on the handpiece, it is impossible for the user to set wrong parameters for a tool, e.g., the maximum allowed rotational speed or torque.

Another advantage is the possibility of selecting a partial data volume from a first data volume for programming the handpiece. A comprehensive preselection on the handpiece is ensured by transmitting just a partial data volume, in particular the data sets of the files being used by the user. In addition, a complete data volume is available to the user for preferably all the files obtainable on the market.

The first data volume in the second memory is guaranteed to be up-to-date by another memory, in particular a memory card. By loading the second memory by means of an additional memory, the data volume may be updated and completed constantly with new data sets.

Within the scope of this application, it is understandable that the present method and device for programming a handpiece are not limited to the handpieces for root canal treatment specified in the description. Instead, additional handpieces may be programmed for general treatment in the medical field, in particular in the dental field.

These and other embodiments are explained in greater detail below on the basis of exemplary embodiments and in conjunction with the accompanying drawings.

DETAILED DESCRIPTION

Figure 1:
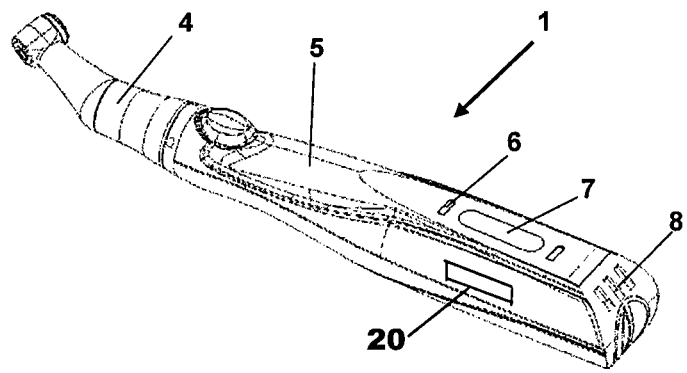
FIG. 1 shows a cordless handpiece for root canal treatment having a first memory comprising an instrument part and a main part.

FIG. 1 shows a cordless handpiece 1, preferably for root canal treatment. The handpiece 1 consists of an instrument part 4 and a main part 5. The main part 5 forms the drive unit for the cordless handpiece 1. In addition to the drive motor with an output shaft for coupling the instrument part 4, a battery (not shown), which is used to supply electric power to the motor, is provided in the handpiece. For charging the battery, charging contacts 8 are provided on the main part 5. In addition, a control and a first memory 20 are arranged in the main part 5 for storing a partial data volume transmissible to the handpiece 1. A data set is selected from the partial data volume by at least one control element 6 and a display 7. The handpiece also has a data receiving unit for transmitting a partial data volume from the base station 2 or from an additional memory 3 to the handpiece 1. This interface is preferably designed as a wired interface via the charging contacts 8 or via additional electric contacts (not shown). The instrument part 4 serves to transmit the drive movement from the output shaft of the drive motor to the tool.

Figure 2:
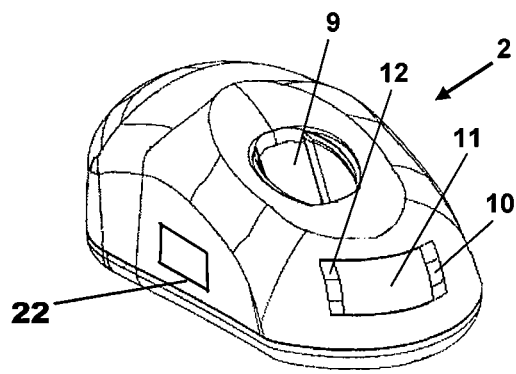
FIG. 2 shows a base station having a second memory for receiving the cordless handpiece, in particular for supplying power to the handpiece.

FIG. 2 shows a base station 2 corresponding to the cordless handpiece 1. The base station 2 is preferably designed as a charger for the cordless handpiece 1. A charging circuit for charging the battery in the handpiece 1 is provided in the base station 2. To this end, the handpiece 1 is connected to the base station 2, e.g., by inserting the handpiece 1 in a receptacle 9. In addition, a control and a second memory 22 are also provided on the base station 2. This second memory 22 serves to provide the first data volume. By means of the at least one control element 10 as well as the display 11 on the base station, the user may select a partial data volume to be transmitted to the handpiece 1. In addition to the control element 10, other control elements 12 may also be arranged on the base station 2 for setting additional functions of the tool and handpiece. For transmission of a partial data volume from an external memory, such as a third memory 3 (described below)

to the base station 2 (second memory 22), and from the base station 2 (second memory 22) to the handpiece, the base station 2 has a data receiving and transmitting unit (not shown). The base station 2 can include an interface between the third memory 3 and the base station 2, such as one configured for a wired connection, in particular a receptacle for a memory card, a port for a standardized or proprietary connector (e.g., a USB port) or another form of physical interface providing a wired connection.

Figure 3:
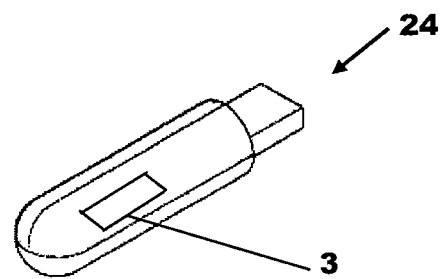
FIG. 3 shows an additional memory for loading the memory in the base station and/or the memory in the handpiece.

FIG. 3 shows an example of the third memory 3, which as illustrated is embodied as a portable memory element 24 (e.g., a USB stick). Alternatively, the third memory 3 could be embodied as, e.g., a Smart Media card, memory stick, multimedia card or Secure Digital memory card (SD card or mini-SD card). The third memory 3 serves to transmit data sets to the base station 2 or directly to the handpiece 1, if the handpiece is provided with a suitable interface for connection to the third memory 3.

For embodiments in which there is no second memory in the base station, the second memory can be embodied as a portable memory element (such as shown in FIG. 3.

This application is not limited to the exemplary embodiments described herein. Within the scope of the invention, it is of course self-evident that data may be transmitted from the base station 2 to the handpiece 1 or from the additional, in particular third, memory 3 to the base station 2 or directly to the handpiece 1 by wireless data transmission. To this end, the transmission is preferably accomplished by means of radiofrequency waves, infrared, wireless or inductive or capacitive data transmission.

What is claimed is:

1. A method for operating a cordless handpiece used for root canal treatment and having a first memory, at least one handpiece control element, a display and a tool holder for a treatment tool, comprising:
   providing a first data volume having a plurality of data sets in a second memory separate from the first memory, each of the data sets in the second memory comprising predetermined associated parameters in a multi-field format comprising parameters assigned to the cordless handpiece and/or to an associated set of one or more treatment tools,
   selecting multiple data sets from the plurality of data sets of the first data volume in the second memory,
   transmitting the selected multiple data sets from the second memory to the first memory to update the first memory of the handpiece,
   using the handpiece to select one of the multiple data sets for a desired treatment tool from the updated first memory for operation of the handpiece (1) manually by actuating the at least one handpiece control element arranged on the handpiece to select from the multiple data sets displayed on the display or (2) automatically with automatic tool identification on the handpiece, and
   modifying the selected one of the data sets by using the handpiece control element to modify at least one parameter of the selected one of the data sets,
   wherein there is at least one remaining data set in the updated first memory that remains unselected while the selected one of the data sets is in use.

2. The method according to claim 1, wherein the multiple data sets are transmitted from the second memory to the first memory of the handpiece by a wired connection.

3. The method according to claim 1, wherein the multiple data sets are transmitted from the second memory to the first memory of the handpiece by a wired connection comprising electrical contacts.

4. The method according to claim 1, wherein the multiple data sets are transmitted wirelessly from the second memory to the first memory of the handpiece.

5. The method according to claim 1, wherein the multiple data sets are transmitted wirelessly from the second memory to the first memory of the handpiece by at least one of a radio, radio frequency, infrared, inductive or capacitive data transmission.

6. The method according to claim 1, wherein the second memory is updatable with multiple data sets from a third memory.

7. The method according to claim 6, wherein the second memory is updatable with multiple data sets from a third memory by a wired connection between the second memory and the third memory.

8. The method according to claim 6, wherein the second memory is updatable with multiple data sets from a third memory by a wireless connection between the second memory and the third memory.

9. The method according to claim 1, wherein at least one of the first memory and the second memory comprises a memory card.

10. The method according to claim 1, wherein selecting multiple data sets from the first data volume of the second memory comprises actuating at least one control element, the at least one control element comprising at least one of the handpiece control element, a control element positioned on a base station and/or a control element positioned on a memory element.

11. The method according to claim 1, wherein the predetermined associated parameters in the multi-field format comprise a treatment tool parameter comprising a tool rotational speed or a tool torque.

12. The method according to claim 1, wherein the predetermined associated parameters in the multi-field format comprise a handpiece parameter comprising at least one handpiece autofunction parameter selected from a group comprising autoreverse, autostop and autoforward parameters.

13. The method according to claim 1, wherein the predetermined associated parameters in the multi-field format comprise a treatment tool designation parameter comprising a tool name associated with a respective tool.

14. The method according to claim 1, wherein selecting the data set with automatic tool identification comprises identifying a treatment tool installed in the tool holder of the handpiece with at least one of radiofrequency waves, RFID, barcode scanning and at least one sensor.

15. The method according to claim 1, wherein the second memory is associated with a base station.

16. The method according to claim 1, wherein the second memory comprises a portable memory element.

17. The method of claim 1, further comprising displaying the multiple data sets on the display serially or simultaneously.

18. The method of claim 1, wherein each of the data sets in the second memory comprises at least two parameters assigned to the cordless handpiece and/or to the treatment tool.

19. The method according to claim 1, wherein modifying the selected one of the data sets by using the handpiece control element to modify at least one parameter comprises changing a state of a root canal measurement switch or changing the state of a torque reducing switch.

20. A cordless handpiece used for root canal treatment and a device for programming the cordless handpiece, comprising:

a cordless handpiece comprising a first memory, a display and a tool holder for a treatment tool, and a device comprising a second memory separate from the first memory of the handpiece, the second memory having a first data volume comprising a plurality of data sets, each of the data sets comprising a plurality of predetermined associated parameters in a multi-field format comprising parameters assigned to the cordless handpiece and/or to an associated set of one or more treatment tools, at least one control element operable to select multiple data sets from the first data volume and operable to cause the selected multiple data sets to be transmitted from the second memory to the first memory of the handpiece to update the first memory, wherein the handpiece comprises a handpiece control element arranged on the handpiece manually operable to select one data set from the multiple data sets of the updated first memory displayed on the display or a tool identification circuit in the handpiece automatically operable to identify a tool installed in the tool holder, the identification circuit identifying an installed treatment tool and automatically selecting one data set from multiple data sets of the updated first memory based on the installed treatment tool, wherein there is at least one remaining data set in the updated first memory that remains unselected while the handpiece is operated with the selected data set in use, and wherein the handpiece control element is further operable to modify the selected data set by modifying at least one parameter of the selected data set.

21. The cordless handpiece and device according to claim 20, wherein the second memory comprises electrical contacts for establishing a wired connection, and the second memory is operable to cause the selected multiple data sets to be transmitted from the second memory to the first memory via the wired connection.

22. The cordless handpiece and device according to claim 20, wherein the second memory is operable to cause the selected multiple data sets to be transmitted wirelessly from the second memory to the first memory.

23. The cordless handpiece and device according to claim 20, further comprising a third memory, and wherein the third memory is operable to update the second memory with multiple updated data sets.

24. The cordless handpiece and device according to claim 20, wherein the handpiece control element is operable to modify a state of a root canal measurement switch or a torque reducing switch.

25. A cordless handpiece used for root canal treatment and a device for programming the cordless handpiece, comprising:

a cordless handpiece comprising a first memory, display means for displaying information and a tool holder for a treatment tool, and a device comprising a second memory separate from the first memory of the handpiece, the second memory having a first data volume comprising a plurality of data sets, each of the data sets comprising a plurality of predetermined associated parameters in a multi-field format comprising parameters assigned to the cordless handpiece and/or to an associated set of one or more treatment tools, at least one control element operable to select multiple data sets from the first data volume and operable to cause the selected multiple data sets to be transmitted from the second memory to the first memory of the handpiece to update the first memory, wherein at least two of the multiple data sets in the updated first memory relate to the same treatment tool, wherein the handpiece comprises a handpiece control element arranged on the handpiece manually operable to select one data set from the multiple data sets of the updated first memory displayed on the display means or a tool identification circuit in the handpiece automatically operable to identify a tool installed in the tool holder, the identification circuit identifying an installed treatment tool and automatically selecting one data set from multiple data sets of the updated first memory based on the installed treatment tool, wherein there is at least one remaining data set in the updated first memory that remains unselected while the handpiece is operated with the selected data set in use, and wherein the handpiece control element is further operable to modify the selected data set by modifying at least one parameter of the selected data set.

26. The cordless handpiece and device according to claim 25, wherein the handpiece control element is operable to modify a state of a root canal measurement switch or a torque reducing switch.

* * * * *